(12) United States Patent
Wegner et al.

(10) Patent No.: US 10,786,436 B2
(45) Date of Patent: *Sep. 29, 2020

(54) ALCOHOL BASED SANITIZER WITH IMPROVED DERMAL COMPATIBILITY AND FEEL

(71) Applicant: ECOLAB USA INC., Saint Paul, MN (US)

(72) Inventors: Joseph R. Wegner, Saint Paul, MN (US); Cheryl A. Littau, Saint Paul, MN (US)

(73) Assignee: Ecolab USA Inc., Saint Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/435,120

(22) Filed: Jun. 7, 2019

(65) Prior Publication Data

US 2019/0290561 A1 Sep. 26, 2019

Related U.S. Application Data

(63) Continuation of application No. 15/951,422, filed on Apr. 12, 2018, now Pat. No. 10,588,836, which is a continuation of application No. 15/235,428, filed on Aug. 12, 2016, now Pat. No. 9,962,323, which is a continuation of application No. 13/911,524, filed on Jun. 6, 2013, now Pat. No. 9,439,841.

(51) Int. Cl.
| | |
|---|---|
| *A61K 8/34* | (2006.01) |
| *A61K 8/37* | (2006.01) |
| *A61Q 19/10* | (2006.01) |
| *A61K 8/891* | (2006.01) |
| *A61K 8/04* | (2006.01) |
| *A61K 8/365* | (2006.01) |
| *A61K 8/44* | (2006.01) |
| *A61K 8/49* | (2006.01) |
| *A61K 8/67* | (2006.01) |
| *A61K 8/893* | (2006.01) |
| *A61Q 17/00* | (2006.01) |
| *A61K 31/045* | (2006.01) |
| *A61K 31/455* | (2006.01) |

(52) U.S. Cl.
CPC .......... *A61K 8/34* (2013.01); *A61K 8/042* (2013.01); *A61K 8/345* (2013.01); *A61K 8/365* (2013.01); *A61K 8/37* (2013.01); *A61K 8/375* (2013.01); *A61K 8/44* (2013.01); *A61K 8/4913* (2013.01); *A61K 8/4926* (2013.01); *A61K 8/678* (2013.01); *A61K 8/891* (2013.01); *A61K 8/893* (2013.01); *A61Q 17/005* (2013.01); *A61Q 19/10* (2013.01); *A61K 31/045* (2013.01); *A61K 31/455* (2013.01); *A61K 2800/592* (2013.01)

(58) Field of Classification Search
CPC ............................ A61K 31/045; A61K 31/455
USPC ................................................. 514/724, 455
See application file for complete search history.

(56) References Cited

U.S. PATENT DOCUMENTS

| | | |
|---|---|---|
| 3,787,566 A | 1/1974 | Gauvreau |
| 3,938,810 A | 2/1976 | Pradervand |
| 4,096,240 A | 6/1978 | Mathur |
| 4,220,665 A | 9/1980 | Klein |
| 4,336,151 A | 6/1982 | Like et al. |
| 4,511,486 A | 4/1985 | Shah |
| 4,714,568 A | 12/1987 | Hurnik et al. |
| 4,857,302 A | 8/1989 | Decker, Jr. et al. |
| 5,015,228 A | 5/1991 | Columbus et al. |
| 5,047,249 A | 9/1991 | Rothman et al. |
| 5,073,371 A | 12/1991 | Turner et al. |
| 5,167,950 A | 12/1992 | Lins |
| D338,585 S | 8/1993 | Bell et al. |
| 5,254,331 A | 10/1993 | Mausner |
| 5,256,401 A | 10/1993 | Duckenfield et al. |
| 5,265,772 A | 11/1993 | Bartasevich et al. |
| 5,266,598 A | 11/1993 | Ninomiya et al. |
| D343,751 S | 2/1994 | Bell et al. |
| D346,332 S | 4/1994 | Kanfer et al. |
| 5,335,373 A | 8/1994 | Dangman et al. |
| 5,336,497 A | 8/1994 | Guerrero et al. |
| 5,370,267 A | 12/1994 | Schroeder |
| 5,441,178 A | 8/1995 | Wysocki |
| 5,443,236 A | 8/1995 | Bell et al. |
| 5,449,137 A | 9/1995 | Bell et al. |
| 5,462,688 A | 10/1995 | Lippman et al. |
| D365,509 S | 12/1995 | Bell et al. |
| D365,518 S | 12/1995 | Wysocki |
| D365,755 S | 1/1996 | Kanfer et al. |
| 5,523,014 A | 6/1996 | Dolan et al. |
| 5,558,453 A | 9/1996 | Bell et al. |
| 5,587,358 A | 12/1996 | Sukigara et al. |
| 5,625,659 A | 4/1997 | Sears |
| 5,629,006 A | 5/1997 | Hoang et al. |
| 5,635,462 A | 6/1997 | Fendler et al. |
| D383,001 S | 9/1997 | Bell et al. |
| D385,795 S | 11/1997 | Wysocki et al. |

(Continued)

FOREIGN PATENT DOCUMENTS

| | | |
|---|---|---|
| DE | 19523320 A1 | 1/1997 |
| EP | 0396422 B1 | 11/1990 |

(Continued)

OTHER PUBLICATIONS

Bissett, Donald L., et al., "Miacinamide: A B Vitamin that Improves Aging Facial Skin Appearance", Dermatology Surgery 2005, 31, pp. 860-865. 2000.

(Continued)

*Primary Examiner* — Kevin E Weddington
(74) *Attorney, Agent, or Firm* — McKee, Voorhees & Sease, PLC

(57) ABSTRACT

Applicants have identified a critical skin benefit package that can be used in liquid alcohol sanitizing compositions that provides lower amounts of skin conditioners in combination with a specific ratio of different emollients that provide improved skin health with chronic repeated use. The package also provides improved skin feel with without a tacky residue upon drying.

20 Claims, 8 Drawing Sheets

(56) References Cited

U.S. PATENT DOCUMENTS

| | | |
|---|---|---|
| 5,718,353 A | 2/1998 | Kanfer et al. |
| 5,719,113 A | 2/1998 | Fendler et al. |
| D392,136 S | 3/1998 | Ross et al. |
| 5,725,131 A | 3/1998 | Bell et al. |
| D400,799 S | 11/1998 | Bell et al. |
| 5,833,998 A | 11/1998 | Biedermann et al. |
| 5,902,778 A | 5/1999 | Hartmann et al. |
| D411,456 S | 6/1999 | Mast et al. |
| 5,939,082 A | 8/1999 | Oblong et al. |
| 5,944,227 A | 8/1999 | Schroeder et al. |
| D415,343 S | 10/1999 | Maddox |
| 5,962,482 A | 10/1999 | Bissett |
| 5,968,528 A | 10/1999 | Deckner et al. |
| 5,972,356 A | 10/1999 | Peffly et al. |
| D416,417 S | 11/1999 | Ross et al. |
| 5,980,921 A | 11/1999 | Biedermann et al. |
| 5,996,851 A | 12/1999 | Dolan et al. |
| 5,997,887 A | 12/1999 | Ha et al. |
| 5,997,890 A | 12/1999 | Sine et al. |
| D418,708 S | 1/2000 | Kanfer et al. |
| 6,022,551 A | 2/2000 | Jampani et al. |
| 6,024,942 A | 2/2000 | Tanner et al. |
| D422,828 S | 4/2000 | Kanfer et al. |
| 6,065,639 A | 5/2000 | Maddox et al. |
| 6,090,395 A | 7/2000 | Asmus et al. |
| 6,130,253 A | 10/2000 | Franklin et al. |
| 6,183,761 B1 | 2/2001 | Bisset et al. |
| 6,183,766 B1 | 2/2001 | Sine et al. |
| 6,217,885 B1 | 4/2001 | Roder et al. |
| 6,224,888 B1 | 5/2001 | Vatter et al. |
| 6,265,363 B1 | 7/2001 | Viscovitz |
| 6,267,976 B1 | 7/2001 | Barnhart et al. |
| 6,274,124 B1 | 8/2001 | Vollhardt |
| 6,309,657 B2 | 10/2001 | Vatter et al. |
| 6,319,958 B1 | 11/2001 | Johnson et al. |
| 6,333,039 B1 | 12/2001 | Fendler et al. |
| 6,352,701 B1 | 3/2002 | Scholz et al. |
| 6,383,505 B1 | 5/2002 | Kaiser et al. |
| 6,383,997 B1 | 5/2002 | McManus |
| 6,423,329 B1 | 7/2002 | Sine et al. |
| 6,472,356 B2 | 10/2002 | Narula et al. |
| 6,534,069 B1 | 3/2003 | Asmus et al. |
| 6,592,880 B1 | 7/2003 | Jager |
| 6,689,593 B2 | 2/2004 | Millis et al. |
| 6,709,647 B2 | 3/2004 | Bhakoo et al. |
| 6,723,689 B1 | 4/2004 | Hoang et al. |
| 6,846,846 B2 | 1/2005 | Modak et al. |
| 6,939,552 B2 | 9/2005 | Ansara et al. |
| 6,977,082 B2 | 12/2005 | Seitz, Jr. et al. |
| 7,166,435 B2 | 1/2007 | Rosenbloom |
| 7,199,090 B2 | 4/2007 | Koivisto et al. |
| 7,842,725 B2 | 11/2010 | Wegner et al. |
| 7,883,487 B2 | 2/2011 | Shantha et al. |
| 8,058,315 B2 | 11/2011 | Wegner et al. |
| 8,338,491 B2 | 12/2012 | Asmus et al. |
| 8,383,686 B2 | 2/2013 | Wegner et al. |
| 9,439,841 B2 * | 9/2016 | Wegner .................... A61K 8/34 |
| 9,962,323 B2 * | 5/2018 | Wegner .................... A61K 8/34 |
| 10,588,836 B2 * | 3/2020 | Wegner .................... A61K 8/893 |
| 2002/0022660 A1 | 2/2002 | Jampani et al. |
| 2003/0215475 A1 | 11/2003 | Shah et al. |
| 2004/0102429 A1 | 5/2004 | Modak et al. |
| 2004/0191274 A1 | 9/2004 | Grayson et al. |
| 2004/0247685 A1 | 12/2004 | Modak et al. |
| 2005/0271595 A1 | 12/2005 | Brown |
| 2006/0104911 A1 | 5/2006 | Novak |
| 2006/0104919 A1 | 5/2006 | Novak |
| 2006/0182690 A1 | 8/2006 | Veeger et al. |
| 2006/0204466 A1 | 9/2006 | Littau et al. |
| 2006/0239947 A1 | 10/2006 | Dias et al. |
| 2006/0281663 A1 | 12/2006 | Asmus |
| 2007/0027055 A1 | 2/2007 | Koivisto et al. |
| 2007/0065383 A1 | 3/2007 | Fernandez de Castro et al. |
| 2007/0148101 A1 | 6/2007 | Snyder et al. |
| 2007/0179207 A1 | 8/2007 | Fernandez de Castro et al. |
| 2007/0258911 A1 | 11/2007 | Fernandez de Castro et al. |
| 2009/0191248 A1 | 7/2009 | Hoffman et al. |
| 2009/0041820 A1 | 9/2009 | Wu et al. |
| 2009/0324661 A1 | 12/2009 | Polonka et al. |
| 2010/0159028 A1 | 6/2010 | Shultz |
| 2010/0282409 A1 | 11/2010 | Hobbs et al. |
| 2012/0214878 A1 | 8/2012 | Korb et al. |
| 2013/0090380 A1 | 4/2013 | Heisig et al. |
| 2013/0137777 A1 | 5/2013 | Wegner et al. |

FOREIGN PATENT DOCUMENTS

| | | |
|---|---|---|
| EP | 0849070 A1 | 6/1998 |
| EP | 0882446 A1 | 12/1998 |
| GB | 2230186 A | 10/1990 |
| GB | 2414666 A | 12/2005 |
| KR | 1020050073141 | 7/2005 |
| WO | 2005051341 | 6/2005 |
| WO | 2006094387 | 9/2006 |

OTHER PUBLICATIONS

Brehm-Stecher, Johnson, "Sensitization of *Staphylococcus aureus* and *Escherichia coli* to Antibiotics by the Sesquiterpenoids Nerolidol, Farnesol, Bisabolol, and Apritone", University of Wisconsin-Madison, Antimicrobial Agents and Chemotherapy, vol. 47, No. 10, p. 3357-3360, 4 pages, Oct. 2003.

Christman MS, Jeremy C., et al., "Two Randomized, Controlled, Comparative Studies of the Stratum Corneum Integrity Benefits of Two Cosmetic Niacinamide/Glycerin Body Moisturizers vs. Conventional Body Moisturizers", Journal of Drugs in Dermatology, vol. 11, Issue 1, pp. 22-29. Jan. 2012.

Kawada, Akira, et al., "Evaluation of anti-wrinkle effects of a novel cosmetic containing niacinamide", Journal of Dermatology 2008, 35, pp. 637-642.

Morton, H., "The relationship of concentration and germicidal efficiency of ethyl alcohol," Annals of the New York Academy of Sciences, vol. 52, pp. 191-196, XP008066591. Aug. 1950.

Schloss Man, M. (Ed.): "The chemistry and manufacture of cosmetics: formulating. vol. 2, Ed. 3", 2000, Allured Pub., USA 277870, XP002390779, p. 237-239.

Technical Information from BASF for Bisabolol, 8 pages. Nov. 2002.

Technical Specification for Farnesol, Symrise, 2 pages. Jun. 1, 2004.

Worldwide Healthcare Inc., "Material Safety Data Sheet." Jan. 24, 2007.

Korean Intellectual Property Office, "International Search Report and The Written Opinion", issued in connection to International Application No. PCT/US2014/037601, 12 pages, dated Sep. 25, 2014.

Ecolab Inc., PCT/IB2009/052871 filed Jul. 1, 2009, "International Search Report", dated Mar. 3, 2010.

* cited by examiner

ALCOHOL BASED SANITIZER WITH IMPROVED DERMAL COMPATIBILITY AND FEEL

CROSS REFERENCE TO RELATED APPLICATIONS

This application is a continuation of application U.S. Ser. No. 15/951,422, filed on Apr. 12, 2018, which is a continuation of U.S. Ser. No. 15/235,428, filed on Aug. 12, 2016, now U.S. Pat. No. 9,962,323, issued May 8, 2018, which is a continuation of application U.S. Ser. No. 13/911,524, filed on Jun. 6, 2013, now U.S. Pat. No. 9,439,841, issued Sep. 13, 2016, all of which are herein incorporated by reference in their entirety.

FIELD OF THE INVENTION

The invention relates to liquid alcohol based skin sanitizing compositions that are formulated for repeated long term use. The compositions include a level of skin heath components to help to maintain or improve skin health while also maintaining an acceptable skin feel and efficiency.

BACKGROUND OF THE INVENTION

Alcohol compositions are desirable hand and skincare products. They are effective against a wide range of microorganisms such as gram positive and gram negative bacteria and fungi. They are also able to kill microorganisms faster than other antimicrobial products. Alcohol antimicrobial products are available as water thin liquids, gels, emulsions, and aerosol foams.

Hand sanitizing substances are intended to reduce the risk of exposure to and the spread of pathogenic microorganisms encountered in day-to-day activities. Although the use of sanitizing alcohol based foams and gels is well known, a need exists for a formulation that will more effectively kill germs and dry quickly, without negatively affecting skin health. However, many such quick drying gels have a composition that leaves an undesirable sticky residue. In addition, if the level of alcohol is increased, such conventional gels often dry the skin. Accordingly, the need persists for a higher percentage of alcohol without generating an undesirable residue or the drying of the skin.

It is well known that skin health can be improved in leave on antibacterial products by the addition of humectants or moisturizers. However, the level of moisturizer needed to improve skin health typically has the drawback of causing excessive product build-up and stickiness which is unpleasant aesthetically to the user, and can also lead to increased difficulty in applying gloves, reducing work efficiency. Both the stickiness and gloving issues may result in reduced product use by healthcare providers because the stickiness tends to make the worker feel their hands are "dirty" and need to be washed and the reduced ability to glove impedes with their work flow.

When the level of skin health components in an alcohol-based sanitizer is not high enough, healthcare workers may experience extreme drying of their hands or in a worse case contact dermatitis, especially in low humidity climates or during the "dry" months of the year. Typical, basic/conventional hand sanitizers do not contain adequate amounts of skin health promoting agents to improve skin health with repeated use.

It is an object of the present invention to provide a liquid alcohol-based skin sanitizing composition that can be in the form of a gel, liquid, emulsion or aerosol foam that provides improved skin feel without sacrificing efficacy and which when used repeatedly will improve skin health.

Other objects of the invention will become clear from the description of the invention which follows.

SUMMARY OF THE INVENTION

Applicants have identified a critical skin benefit package that can be used in liquid alcohol sanitizing compositions that provides improved skin health with chronic repeated use. The package also provides improved skin feel without a tacky residue upon drying.

According to the invention, a skin benefit package of components is employed which includes a specific combination of emollients. The invention uses a combination of "high spreading oils" (such as dicaprylyl carbonate, dibutyl adipate, hexyl laurate, dicaprylyl ether, propylheptyl caprylate, 4-10 centistoke silicone oil, D4, D5, or D6 cyclic siloxane, isocetyl palmitate, hydrogenated polyisobutene, and diethylhexylcarbonate), in combination with medium spreading oils (such as capric/caprylic triglyceride, C12-15 alkyl benzoate, capric triglyceride, caprylic triglyceride, isopropyl myristrate, isopropyl palmitate, octyldodecanol, decyl oleate, cocoglycerides, ethylhexyl stearate, cetearyl isononanoate, cetearyl ethyhexanonate, decyl cocoate, cetyl dimethicone, ethylhexyl palmitate, PPG-11 stearyl ether, PPG-15 stearyl ether, and PPG-14 butyl ether). The ratio of oils is from about 3:1 to about 1:3 high spreading oil to medium spreading oil.

The skin benefit package also includes skin conditioning agents such as glycerin, bisabolol, vitamin E, nicatinamide, gluconic acid, glycine and the like. The skin conditioning agents are present in an amount of less than 1.0 wt. % each, preferably less than 0.8 wt. % each and more preferably less than 0.5 wt. % each and all skin conditioning agents together comprise less than 3 wt. % of the total sanitizing composition, preferably less than 2 wt. % and more preferably less than 1 wt. %.

The liquid alcohol sanitizing product may be in the form of a water thin liquid, gel, emulsion, or foam (aerosol or non-aerosol). In a preferred embodiment, the product is in the form of a non-aerosol foaming sanitizer.

In addition to the skin benefit package, the composition includes a sanitizing component of a linear or branched lower alcohol, such as a $C_{1-6}$ alcohol, or a mixture of two or more such alcohols. The alcohol is present in an efficacious amount, generally from about 40% to about 99%, by weight of active alcohol, preferably from about 50 to about 90 wt. %, and most preferably from about 60 to about 80 wt. %. Examples of suitable alcohols include ethanol, propanols, such as isopropanol and n-propanol, and butanols.

The composition can also include other components such as other skin conditioners, emollients, moisturizers, humectants, thickeners, surfactants, fragrance, water and the like.

The invention also includes a method of sanitizing skin by applying the sanitizer to the skin and allowing the sanitizer to dry. The method is particularly designed for multiple use settings, such as healthcare, where workers may apply the composition multiple times a day. The method includes use of a composition that includes lower amount of skin health materials applied multiple times a day (chronic dosing) and has similar affects as higher levels applied once or twice a day (acute dosing).

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF THE FIGURES

Figure 3:
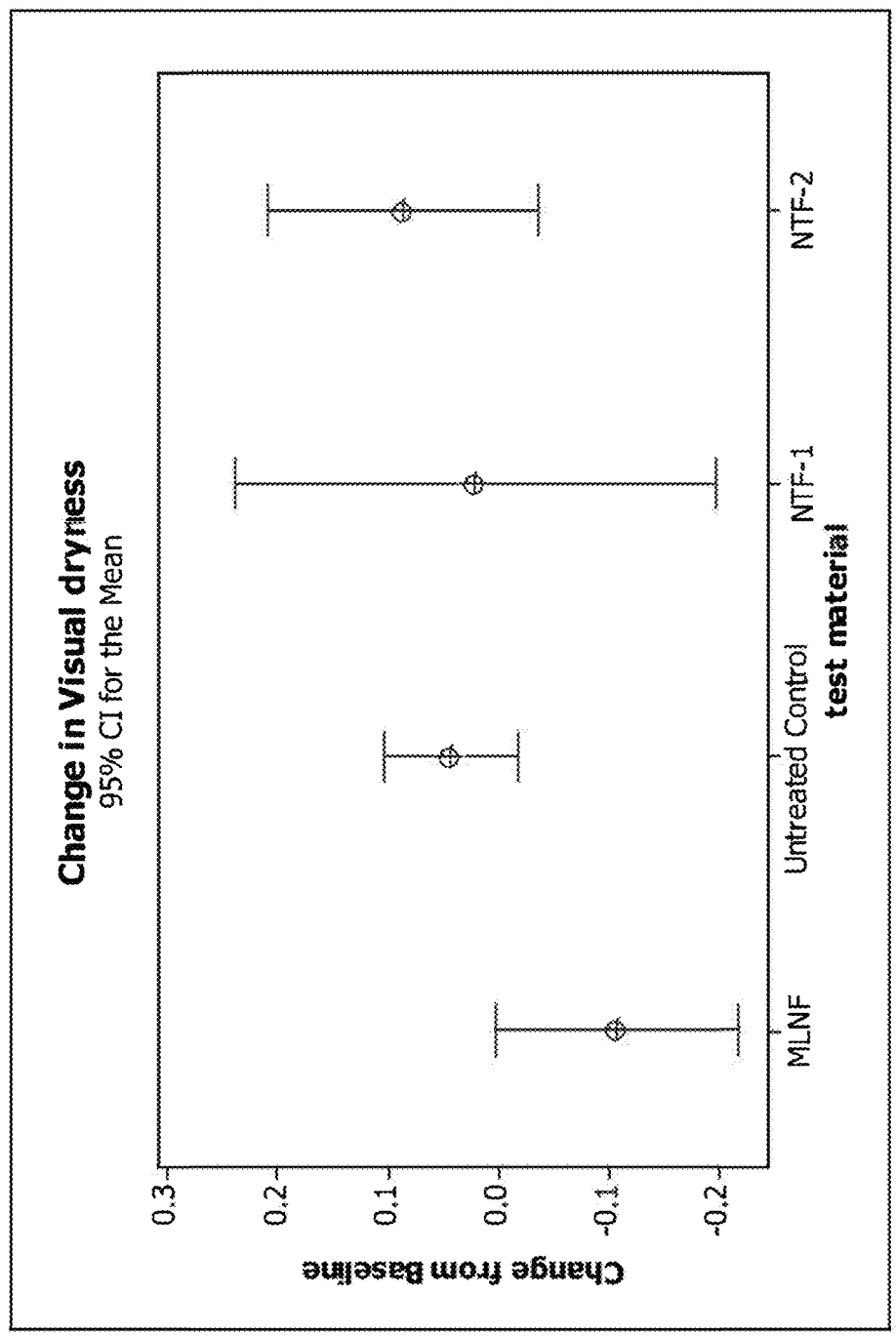

FIG. 3 is a graph of a forearm controlled application test (FCAT) showing change in visual dryness for 2 compositions of the invention and the commercially available skin nourishing formula, as well as untreated skin. From the results one can see that the products were all similar with respect to change in visual dryness despite the fact that the compositions of the invention had lower levels of skin conditioning components.

Figure 4:
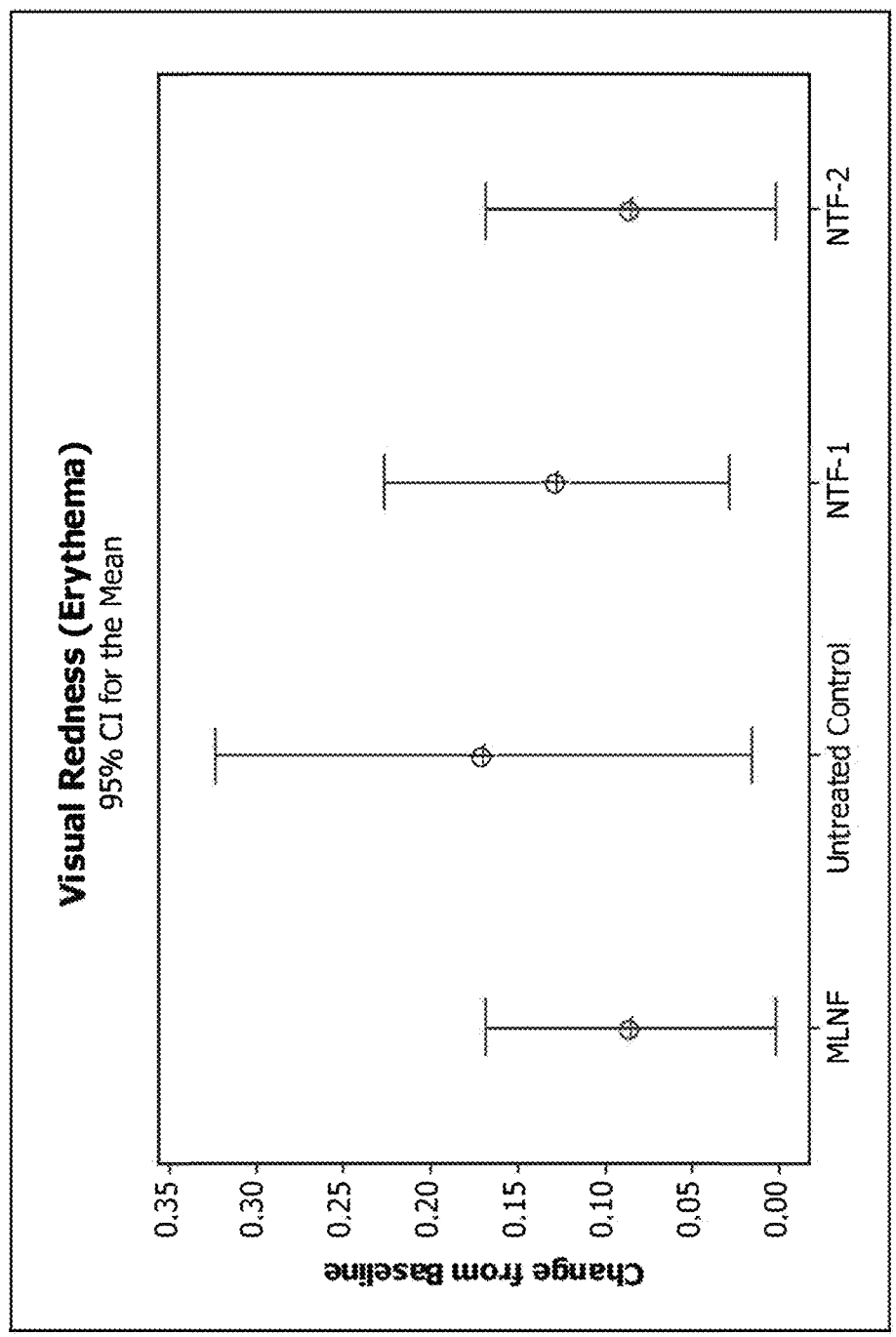

FIG. 4 is a graph of results of the FCAT showing change versus baseline for visual redness. Here again, all of the products were statistically similar despite the fact that the compositions of the invention had less skin conditioning components.

Figure 5:
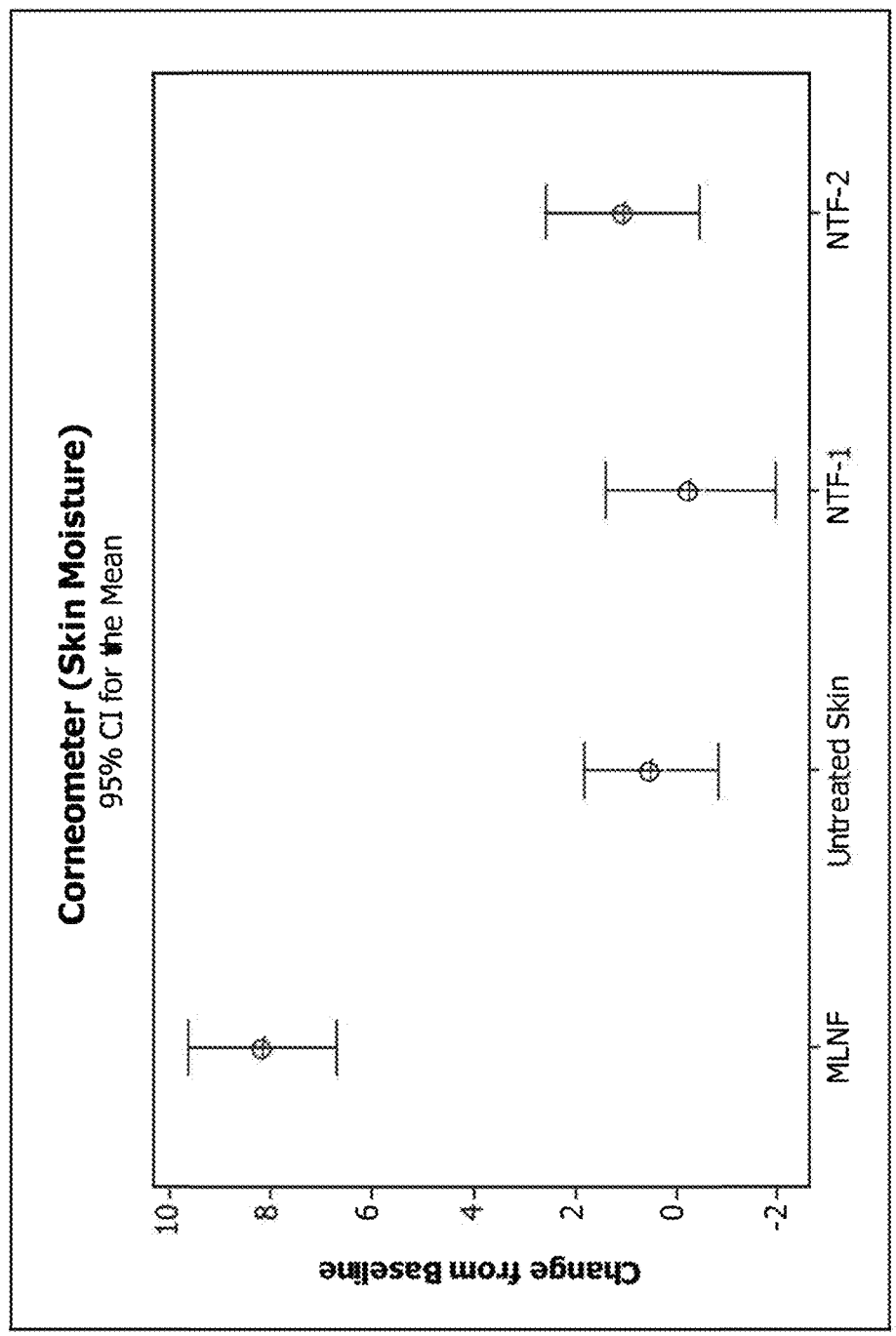

FIG. 5 is a graph of the corneometer (skin moisture) results of the forearm controlled application test. The results show that the compositions of the invention had no deleterious effect on skin moisture.

Figure 6:
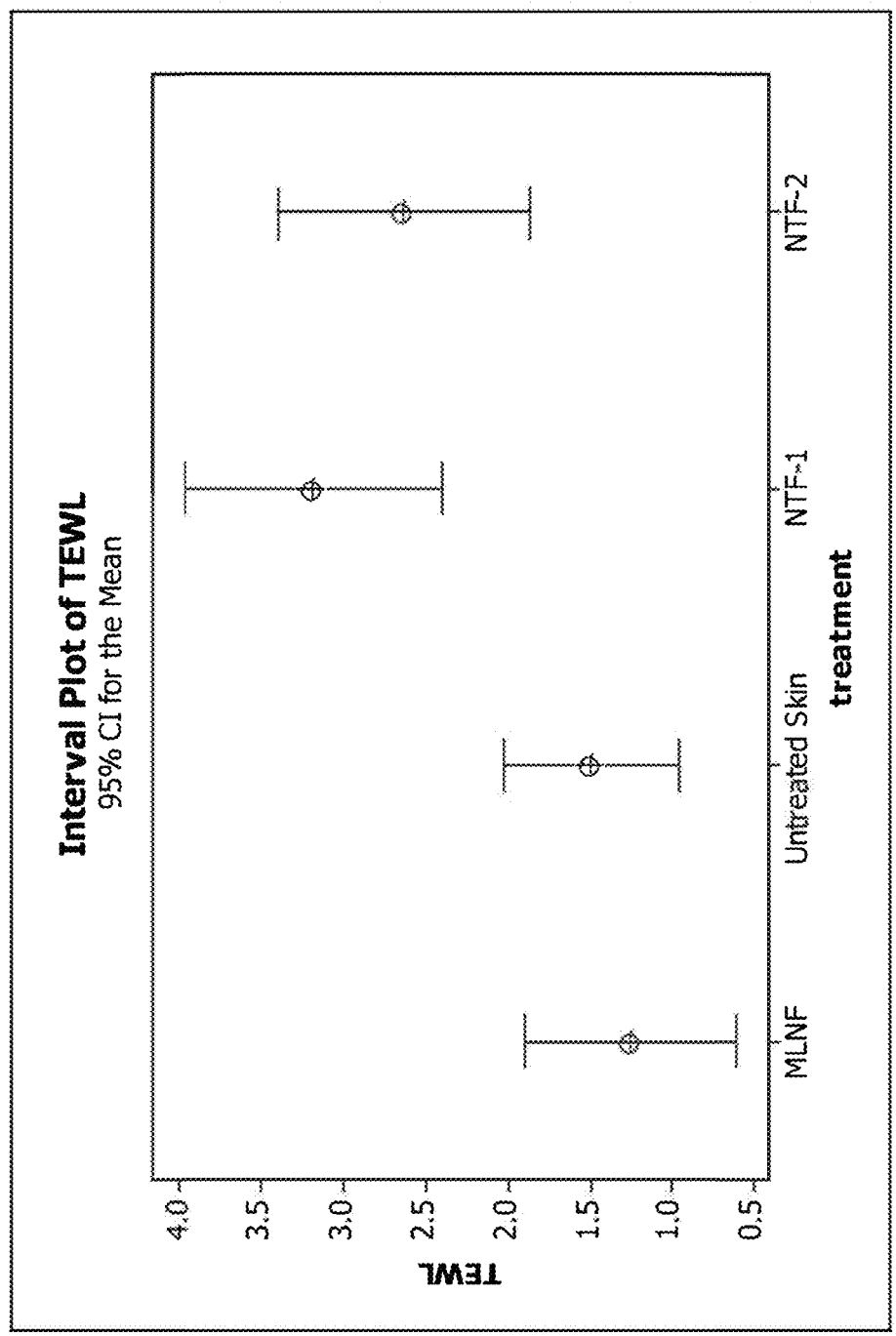

FIG. 6 is a graph of transepidermal water loss (TEWL) results for the forearm controlled application test. The results show that one of the compositions of the invention had statistically different transepidermal water loss.

Figure 7:
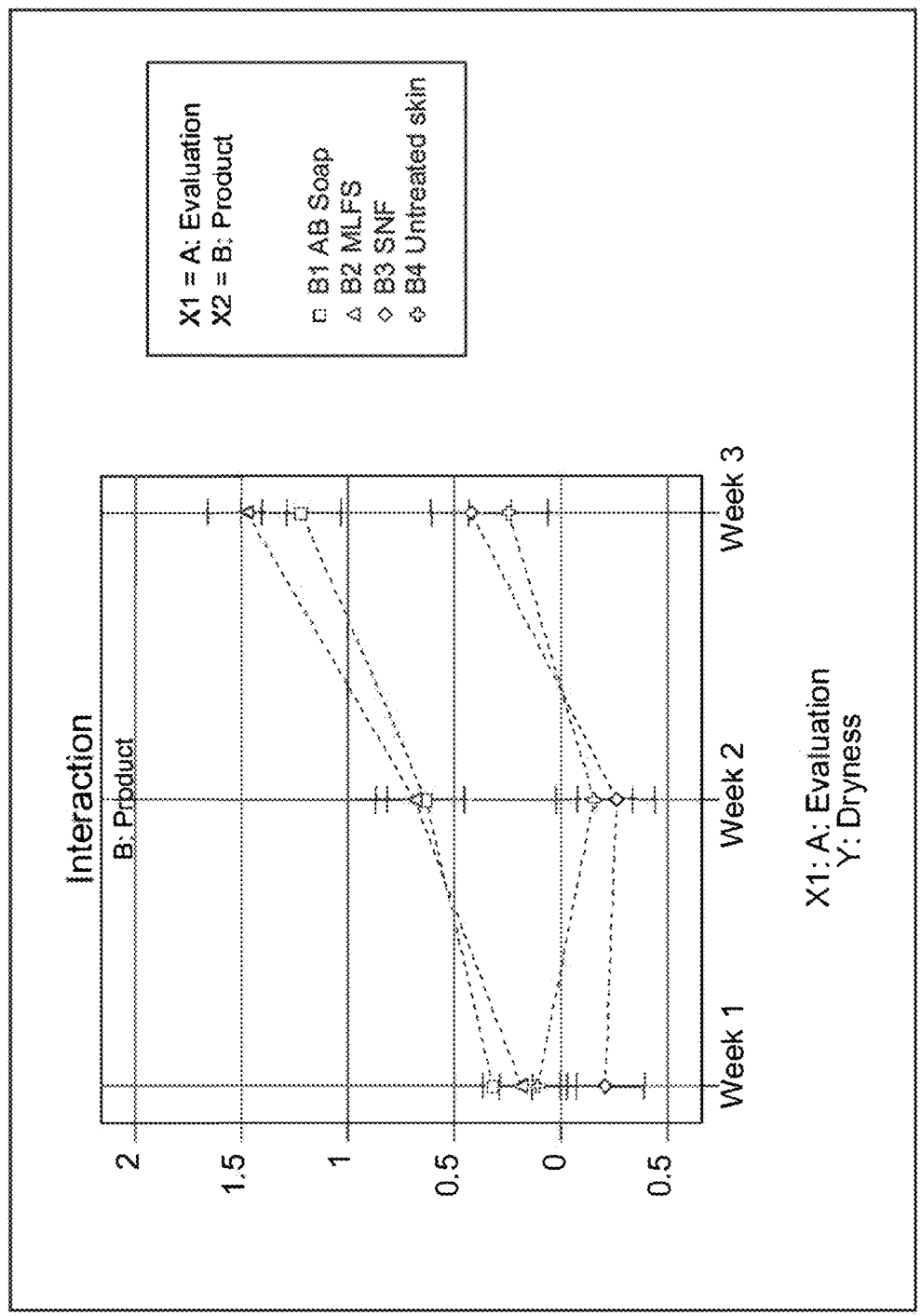

FIG. 7 is a graph of the results of a leg controlled application test (LCAT) showing visual dryness as determined by an expert grader. One can see that the product of the invention even when used at the level of 30 applications per day was most similar to untreated skin while both the commercial "conventional sanitizer at 30 applications per day and antibacterial soap at only 3 washes per day showed significant increase in dryness versus untreated skin.

Figure 8:
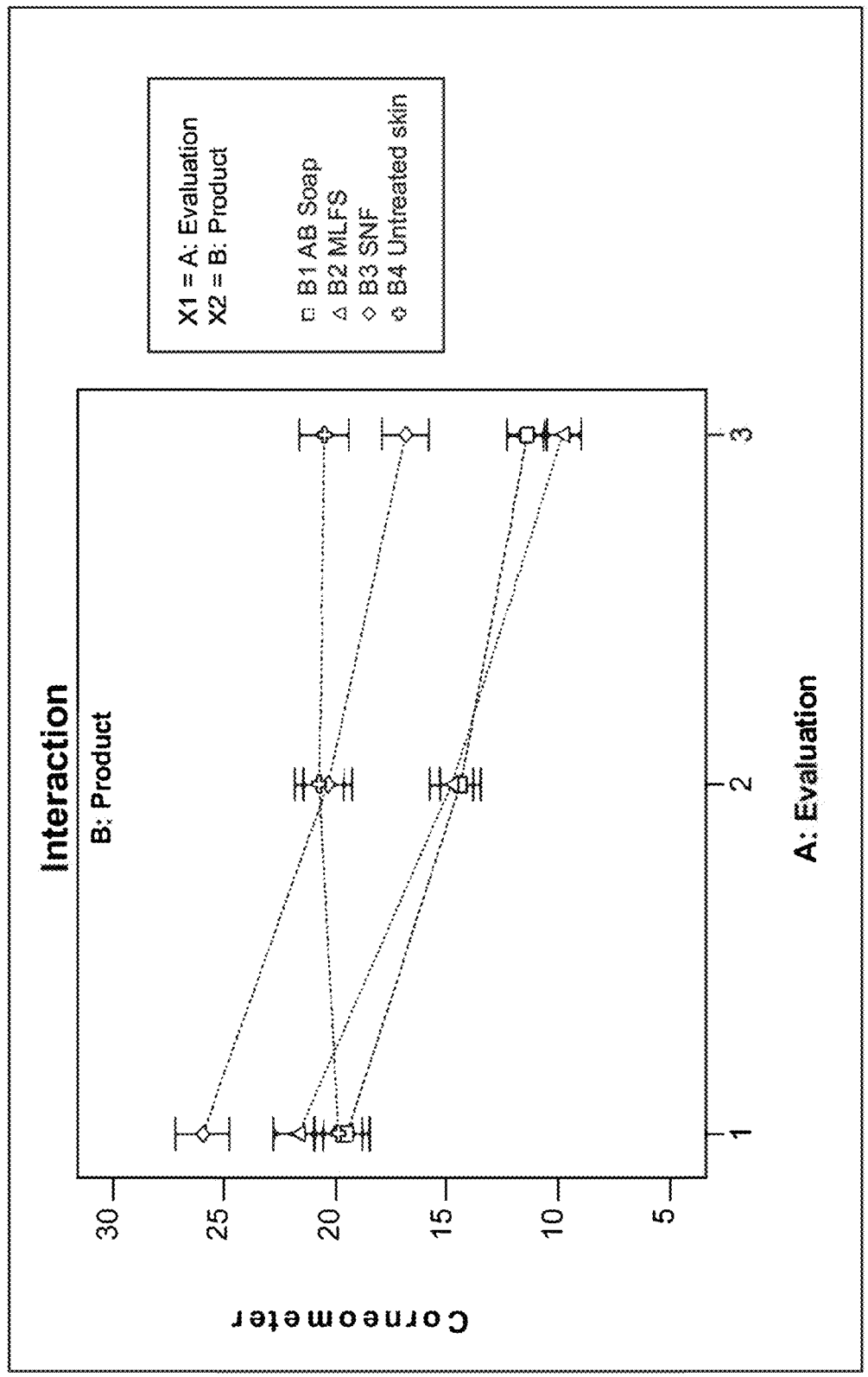

FIG. 8 is a graph of the results of the leg controlled application test showing dryness measured with a corneometer (skin moisture by capacitance). Here again the results show that the composition of the invention demonstrated higher moisture content than skin treated with either of the commercial compositions.

DETAILED DESCRIPTION OF THE INVENTION

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "weight percent," "wt. %," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt. %," etc.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bactericidal and the later, bacteriostatic. A sanitizer and a disinfectant are, by definition, agents which provide antibacterial or bactericidal activity. In contrast, a preservative is generally described as an inhibitor or bacteriostatic composition.

The term "sanitizer," as used herein, refers to an agent that reduces the number of bacterial contaminants to safe levels as judged by public health requirements. The recitation of numerical ranges by endpoints includes all numbers subsumed within that range (e.g., 1 to 5 includes 1, 1.5, 2, 2.75, 3, 3.80, 4, and 5).

The terms "include" and "including" when used in reference to a list of materials refer to but are not limited to the materials so listed.

Skin health can be improved by the addition of humectants or moisturizers to leave-on antibacterial products. However, the level of moisturizer needed to improve skin health typically causes excessive product build-up and stickiness which is unpleasant aesthetically to the user, and can also lead to increased difficulty in applying gloves, reducing work efficiency. Both the stickiness and gloving issues may result in reduced product use by healthcare providers because the stickiness tends to make the worker feel their hands are "dirty" and need to be washed and the reduced ability to glove impedes with their work flow.

When the level of skin health components in an alcohol-based sanitizer is not high enough, healthcare workers may experience extreme drying of their hands or in a worse case contact dermatitis, especially in low humidity climates or during the "dry" months of the year. Typical, basic/conventional hand sanitizers do not contain adequate amounts of skin health promoting agents to improve skin health with repeated use.

There is limited data looking at low dose application of the skin health components such as niacinamide, ceramides, vitamin E, vitamin K, Vitamin D, amino acids (including glycine and proline), applied multiple times a day to reach the same levels that are typically applied in one or two doses in the published clinical studies which have demonstrated improved health with these components. Since healthcare workers apply leave-on products (generally in the form of hand sanitizers) typically ranging from 20 to 100 applications a day, with periodic washes throughout the day, they do not fit into the model of one or two doses of higher active level per day. According to the invention, lower doses of skin health materials applied multiple times a day (chronic) in the correct ratios, can have similar affects as higher dosing once or twice a day (acute).

While skin health is one side of the product acceptance equation, the other side is product feel. If the product is perceived as sticky, tacky, or has high levels of product build-up, the product will not be well accepted by healthcare workers.

As indicated earlier, applicants have identified a critical skin benefit package that can be used in liquid alcohol sanitizing compositions that provides improved skin health with chronic repeated use. The package also provides improved skin feel with without a tacky residue upon drying.

The liquid alcohol sanitizing product may be in the form of a water thin liquid, gel, emulsion, or foam (aerosol or nonaerosol). In a preferred embodiment, the product is in the form of a non-aerosol foaming cleanser.

Compositions of the Invention

The compositions of the invention include a skin benefit package that has a specific ratio of emollients, namely from about 3:1 to about 1:3 of a high spreading oil to a medium spreading oil, which gives the best skin feel without a sticky residue and a lower amount of skin conditioning agents (less than 3 wt. % total) which gives sufficient skin health due to the repeated chronic use of such compositions. The skin benefit package may be added to traditional sanitizing compositions, preferably those that are alcohol based. Thus the composition includes a sanitizing component preferably of a linear or branched lower alcohol, such as a $C_{1-6}$ alcohol, or a mixture of two or more such alcohols. The sanitizing component, is present in an efficacious amount, generally from about 40% to about 99%, by weight of active alcohol, preferably from about 50 to about 90 wt. %, and most preferably from about 60 to about 80 wt. %.

The liquid alcohol sanitizing product may be in the form of a water thin liquid, gel, emulsion, non-aerosol or aerosol foam. In a preferred embodiment, the product is in the form of a non-aerosol foam.

Alcohol

The sanitizing component can include an efficacious amount of a linear or branched lower alcohol. In some embodiments, the alcohol is a lower alkanol, i.e. an alcohol containing 1 to 6 carbon atoms. Typically, these alcohols have antimicrobial properties.

Examples of lower alkanols include, but are not limited to, methanol, ethanol, propanol, butanol, pentanol, hexanol, and isomers and mixtures thereof. In one embodiment, the alcohol comprises ethanol, propanol, or butanol, or isomers or mixtures thereof. In another embodiment, the alcohol comprises ethanol.

Generally, the composition comprises a sanitizing component of alcohol of at least about 30 percent by weight. In certain embodiments, the antimicrobial composition comprises from about 40 weight percent to about 99 weight percent alcohol, in other embodiments, the composition comprises from about 40 weight percent to about 95 weight percent of alcohol, in yet other embodiments, the composition comprises from about 60 weight percent to about 80 weight percent of alcohol, based upon the total weight of the antimicrobial composition.

Skin Benefit Package

The invention includes a skin benefit package to be used with the sanitizing alcohol. According to the invention, the skin benefit package is employed which includes a specific combination of emollients based upon their spreading characteristics as well as skin conditioners. For the purpose of the invention the feel-modifying emollients are characterized into three categories including high spreading, medium spreading, and low spreading. Spreading value of emollients for purposes of the invention is determined by measuring the area covered by a fixed amount of oil over a fixed period of time and is related to a combination of viscosity, polarity, and molecular weight. The preferred method of measurement is that used by Cognis and measures $mm^2$ per 10 minutes.

The high spreading emollients are present in an amount of from about 0 to about 3 wt. %, preferably from about 0-about 2 wt. % and most preferably from about 0 to about 1 wt. %. Medium spreading emollients are present in an amount of from about 0 to about 3 wt. %, preferably from about 0-about 2 wt. % and most preferably from about 0 to about 1 wt. %. Low spreading emollients are presents in an amount of from about 0 to about 5 wt. %, preferably from about 0-about 4 wt. % and most preferably from about 0 to about 3 wt. %.

Applicants have found that the critical feature of the invention is that the ratio of about 3:1 to about 1:3 high spreading oil to medium spreading oil gives the best skin feel without a sticky residue.

High Spreading Emollients

These include materials with spreading values of ≥1000 $mm^2$/10 min. These materials also may include polymers such as dimethyl siloxanes with viscosities less than 10 centistokes (cst). Examples of high spreading oils include but are not limited to dicaprylyl carbonate, dibutyl adipate, hexyl laurate, dicaprylyl ether, propylheptyl caprylate, 4-10 centistoke silicone oil, D4, 5, or 6 cyclic siloxane, isocetyl palmitate, hydrogenated polyisobutene, and diethylhexylcarbonate.

Medium Spreading Emollients

These include materials with spreading values of ≥500 $mm^2$/10 min and <1000 $mm^2$/10 min. These materials also may include polymers such as dimethyl siloxanes with viscosities between 10 cst and 100 cst. Examples of medium spreading oils include but are not limited to capric/caprylic triglyceride, C12-15 alkyl benzoate, capric triglyceride, caprylic triglyceride, isopropyl myristrate, isopropyl palmitate, octyldodecanol, decyl oleate, cocoglycerides, ethylhexyl stearate, ceteraryl isononanoate, cetearyl ethyhexanonate, decyl cocoate, cetyl dimethicone, ethylhexyl palmitate, PPG-11 stearyl ether, PPG-15 stearyl ether, Dimethicone fluid (10-20 cst), and PPG-14 butyl ether.

Low Spreading Emollients

These include spreading values of <500 $mm^2$/10 min and any material oil or waxy material with a melting point greater than 20° C. These materials also may include polymers such as siloxanes with viscosities greater than 100 cst. Low spreading emollients include mono-, di-, and tri-glycerides and butters and hydrogenated versions of seed and nut oils including but not limited to; palm oil, coconut oil, vegetable oil, avocado oil, canola oil, corn oil, soy bean oil, sunflower oil, safflower oil, meadowfoam seed oil, bilberry seed oil, watermelon seed oil, olive oil, cranberry, macadamia nut oil, argan oil, pomegranate oil, argan moraccan oil, blue berry oil, raspberry oil, walnut oil, pecan oil, peanut oil, bayberry oil, mango seed oil, Marula oil, castor oil: Shea butter, jojoba oil, hydrolyzed jojoba oil, Carnauba butter, Carnauba wax, castor isostearate succinate stearyl heptanoate, cetyl ricinoleate, Oleyl frucate, sucrose monostearate, sucrose distearate, sucrose tristearate, sucrose tetrastearate, candela wax, soybean wax, Rapeseed wax, palm wax, bees wax, petrolatum, myristyl myristate, Oleyl Erucate, squalane, stearyl alcohol, Cetearyl isononanoate, polyisobutene, glyceryl stearate, glyceryl distearate, cetyl alcohol, lanolin, lanolin ethoxylate, low molecular weight polyethylene waxes, lower molecular weight polypropylene waxes, PEG-30 glyceryl cocoate, PEG-80 Glyceryl cocoate, PEG-30 Glyceryl stearate, PEG-8 Ricinoleate, PEG-8 Raspberriate, Linear (otherwise known as bis) and Pendent versions of including hydroxyl terminated and methyl ether terminated; PEG-3 to PEG-32 Dimethicone (including but not limited to: PEG-3 Dimethicone, PEG-8 Dimethicone, PEG-9 Dimethicone, PEG-10 Dimethicone, PEG-11 Methyl ether dimethicone, PEG-12 Dimethicone, PEG-14 Dimethicone, PEG-17 Dimethicone, PEG-32 Dimethicone), bis-PEG/PPG-20/20 Dimethicone, PEG/PPG 20/23 Dimethicone, PEG/PPG 20/22 Butyl Ether Dimethicone, PEG/PPG 23/6 Dimethicone, PEG/PPG 20/15 Dimethicone.

Alkyl modified dimethicone (stearoxy dimethicone, behenoxy dimethicone, cetyl dimethicone, certeryl methicone C30-45 Alkyl cetearyl dimethicone copolymer, C30-45 Alkyl dimethicone, caprylyl methicone, PEG-8 dimethicone/dimer dilinoleic acid copolymer, Bis-PEG-10 Dimethicone/Dimer Dilinoleate Copolymer, Stearoxymethicone/Dimethicone Copolymer, Dipheyl dimethicone, Lauryl polyglycerol-3 polydimethylsiloxyethyl dimethicone, Lauryl PEG-9 polydimethylsiloxyethyl dimethicone), Dimethicone fluid (>20 cst), quaternized ammonia silicone polymers, Amino silicones, silicone quaternium-18, Amodimethicone, phenyltrimethicone, amino silicone polyethers, Polyglycerol-3 Disiloxane dimethicone, Polyglycerol-3 polydimethylsiloxyethyl dimethicone, and PEG-9 polydimethylsiloxyethyl dimethicone. Low spreading oils may be present in the composition, but the critical feature is the ratio of high to medium spreading oils.

The ratio of high to medium spreading oils is from about 3:1 to about 1:3 high spreading oil to medium spreading oil. This provides the best health benefits in a chronic application situation while also providing good skin feel with no sticky residue.

Skin Conditioner

The composition can include at least one additional skin conditioner such as vitamins, a humectant, an occlusive agent, or other moisturizer to provide skin moisturizing, skin softening, skin barrier maintenance, anti-irritation, or other skin health benefits. Some non-limiting examples of additional skin conditioners include alkyl benzoate, myristyl myristate, cetyl myristate, gelatin, carboxylic acid, lsactoc acid, glyceryl dioleate, methyl laurate, PPG-9 laurate, lauryl lacylate allantoin, octyl palmitate, lanolin, propylene glycol, butylene glycol, ethylene glycol, caprylyl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, gluconic acid, hydrolyzed silk protein, 1,3-propane-diol, Vitamin E, nicatinamide, stearyl alcohol, isopropyl palmitate, sorbitol, amino acid complexes, panthenol, allantoin, Dihydroxypropyltrimonium Chloride, quaternized hydrolyzed protein such as collagen, oat, wheat, etc . . . , inositol, fructose, sucrose, hydrolyzed plant proteins, seaweed extract, polyethylene glycol, ammonium lactate, sodium hyaluronate, and cyclic peptides.

Some non-limiting examples of humectants include hydroxyethyl urea, agarose, urea, sodium PCA, arginine PCA, fructose, glucose, glutamic acid, glycerine, honey, lactose, maltose, polyethylene glycol, sorbitol and mixtures thereof.

Some non-limiting examples of occlusive agents include petrolatum, shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

The skin conditioner component is present in lower amounts that seen in traditional commercial skin sanitizers. Applicants have found that due to the chronic use of such sanitizers, lower amounts can be used with similar health benefits and less tacky residue. The skin conditioner or combination thereof in total is present in the composition in an amount from about 0.01 wt. % to about 3 wt. %, preferably from about 0.05 wt. % to about 2 wt. %, and more preferably from about 0.1 wt. % to about 1 wt. %. Each individual skin conditioner is present in an amount of no more than 0.5 wt. % to facilitate the skin health for chronic use and best feel characteristics.

Carrier

In some embodiments that composition is water free. In some embodiments there may be a carrier in the present composition, preferably water. It should be appreciated that the water may be provided as deionized water or as softened water. The water provided as part of the concentrate can be relatively free of hardness. It is expected that the water can be deionized to remove a portion of the dissolved solids. That is, the concentrate can be formulated with water that includes dissolved solids, and can be formulated with water that can be characterized as hard water. The amount of water will vary based upon the particular form of the composition, water thin liquid, gel, emulsion, aerosol foam, or non-aerosol foaming cleanser.

Additional Functional Ingredients

Additional functional ingredients may be used to improve the effectiveness of the composition. Some non-limiting examples of such additional functional ingredients include skin feel improvers, skin conditioners, surfactants pH adjusting compound, preservatives, antioxidants, fragrances, dyes, and the like, as well as mixtures thereof.

Terpenoid

The composition may optionally include a terpenoid. Terpenoids are defined as materials with molecular structures containing carbon backbones made up of isoprene (2-methylbuta-1,3-diene) units. Isoprene contains five carbon atoms and therefore, the number of carbon atoms in any terpenoid is a multiple of five. It is believed that terpenoids assist in promoting the uptake of antimicrobial compounds and preservatives by cells of bacteria and fungi, thereby increasing the efficacy of the antimicrobial compound or preservative. See U.S. Pat. No. 6,319,958 and DE 195 23 320 which are incorporated by reference in their entirety. Some non-limiting examples of terpenoids include α-terpinene, cineole, citral, citronellal, citronellol, farnesol, geraniol, limonene, linalool, methone, nerolidol, terpineol, camphene, menthone, myrcene, nerol, tetrayhydrogeraniol, tetrahydrolinalool, apritone, and bisabolol. The terpenoid is preferably farnesol, nerolidol, bisabolol, or apritone.

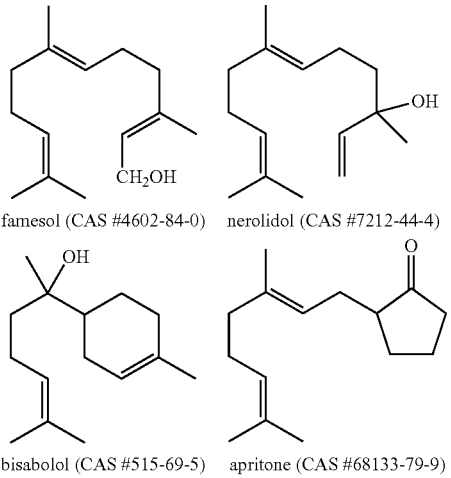

farnesol (CAS #4602-84-0)   nerolidol (CAS #7212-44-4)

bisabolol (CAS #515-69-5)   apritone (CAS #68133-79-9)

The terpenoid is preferably present in the composition in an amount from about 0 to about 1 wt. %, from about 0 to about 0.5 wt. %, and from about 0 to about 0.3 wt. %.

Chelating Agent

The composition may optionally include a chelating agent. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof. Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); N-hydroxyethyl-ethylenediaminetriacetic acid (HEDTA); tetrasodium ethylenediaminetetraacetic acid (EDTA); diethylenetriaminepentaacetic acid (DTPA); and alanine-N,N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, $C_4$-$C_{25}$-mono-or-dicarboxylic acids and $C_4$-$C_{25}$-mono-or-diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelating agent may be present in an amount from about 0 to about 5 wt. %, from about 0 to about 3 wt. %, and from about 0 to about 1.5 wt. %.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

The preservative is preferably present in the composition in an amount from about 0 to about 3 wt. %, from about 0.1 to about 2 wt. %, and from about 0.2 to about 1 wt. %.

Thickener

The composition may optionally include a thickener. Exemplary thickeners include (1) cellulosic thickeners and their derivatives, (2) natural gums, (3) starches, (4) stearates, and (5) fatty acid alcohols, (6) acrylic acid polymers and crosspolymers (example "carbomer", (7) Aristoflex AVC (need generic category name0 Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition. The composition preferably has a viscosity low enough to pump through a foamer such as an Airspray foamer and allow foaming.

Surfactant

PEG-8 to PEG-12 Linear Dimethicone Surfactants

In non-aerosol foaming embodiments, the composition can include a PEG-8 to PEG-12 linear dimethicone surfactants, and in particular PEG-10 linear dimethicone surfactant, are more effective at generating and stabilizing foam in alcohol compositions than dimethicone surfactants with the same PEG chain length but a different polymer architecture.

More particularly it has been discovered that linear block copolymers of PEG with polydimethylsiloxane (specifically with INCI names of PEG-8 dimethicone, PEG-10 dimethicone, and PEG-12 dimethicone) can produce a sufficient foam height to be used as the primary foaming component of a non-aerosol foaming alcohol compositions, which is not the case for copolymers with the same INCI names but different polymer architectures. For example, polymers with pendant PEG groups or other highly branched polymer structures, will not produce sufficient foam to be used as a primary foaming surfactant. In the case of PEG dimethicone copolymers, linear block copolymers refer to when polyethylene glycol chain units are attached to the terminal ends of the linear polydimethylsiloxane backbone:

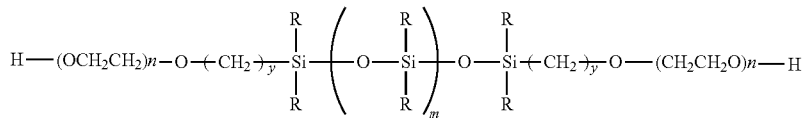

where $R=CH_3$ or $CH_2CH_3$, m=4-20 on average, y=1-5 and n=8-12 on average.

Pendant copolymers refer to linear polydimethylsiloxane polymers with PEG groups attached along the polydimethylsiloxane backbone and may or may not be attached to the terminal chain ends of the polydimethylsiloxane. Such pendant copolymers are often referred to as having a comb or comb-like structure such as:

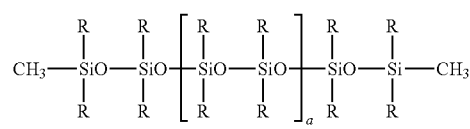

where R is independently=CH$_3$, CH$_2$CH$_3$, or an ethoxylated alkyl chain (for example CH$_2$CH$_2$CH$_2$O(CH$_2$CH$_2$O)$_n$H) attached directly to the silicone end group and a=a repeating silicone group.

Some examples of commercially available PEG-8 to PEG-12 linear dimethicone surfactants include Silsoft 810 (PEG-8) and Silsoft 870 (PEG-12) from Momentive Performance Materials, and Silsurf DI-1010 (PEG-10) from Siltech. In some embodiments, the dimethicone surfactant is preferably a PEG-10 linear dimethicone surfactant.

The dimethicone surfactant can be present in the alcohol composition from about 0.5 to about 10 wt. %, from about 1.0 to about 7 wt. % and from about 2 to about 5 wt. %.

Other Surfactants

The composition may optionally contain a surfactant or surfactant mixture. These can be selected from water soluble or water dispersible nonionic, semi-polar nonionic, anionic, cationic, amphoteric, or zwitterionic surface-active agents; or any combination thereof. The particular surfactant or surfactant mixture chosen for use in the process and products of this invention can depend on the conditions of final utility, including method of manufacture, physical product form, use pH, and the like.

A typical listing of the classes and species of surfactants useful herein appears in U.S. Pat. No. 3,664,961 issued May 23, 1972, to Norris. The disclosure of which is hereby incorporated by reference. Additional surfactants, if present may be in the amount of from 0.5 to about 10 wt. %, from about 1.0 to about 7 wt. % and from about 2 to about 5 wt. %.

Skin Feel Improver

The composition may optionally include a skin feel improver for enhancing the "feel" of the composition on a user's skin or hands. For example, it may be undesirable for a composition to have a scaly or gritty texture when applied to a user's skin or after the multiple applications of the composition. Some non-limiting examples of skin feel improvers include silicone copolymers such as amodimethicone, cyclomethicone, bis-PEG/PPG-20/20 dimethicone, and stearoxytrimethylsilane, naturally occurring or synthetic fatty acid esters or ethers, and polyalkylene glycols.

If a skin feel improver is included, it is preferably present in the composition in an amount from about 0.001 to about 5 wt. %, from about 0.01 to about 3 wt. %, and from about 0.1 to about 2 wt. %.

pH-Adjusting Compound

Sanitizer compositions of the present invention have a pH of about 4.0 to about 8. Within this pH range, the present compositions effectively reduce microbial populations, and are consumer acceptable, i.e., are mild to the skin, are phase stable, and generate copious, stable foam. In some instances a pH adjusting compound may be necessary in a sufficient amount to provide a desired composition pH. To achieve the full advantage of the present invention, the pH-adjusting compound is present in an amount of about 0.05% to about 3.5%, by weight.

Examples of basic pH-adjusting compounds include, but are not limited to, ammonia; mono-, di-, and trialkyl amines; mono-, di-, and trialkanolamines; alkali metal and alkaline earth metal hydroxides; alkali metal phosphates; alkali sulfates; alkali metal carbonates; and mixtures thereof. However, the identity of the basic pH adjuster is not limited, and any basic pH-adjusting compound known in the art can be used. Specific, nonlimiting examples of basic pH-adjusting compounds are ammonia; sodium, potassium, and lithium hydroxide; sodium and potassium phosphates, including hydrogen and dihydrogen phosphates; sodium and potassium carbonate and bicarbonate; sodium and potassium sulfate and bisulfate; monoethanolamine; trimethylamine; isopropanolamine; diethanolamine; and triethanolamine.

The identity of an acidic pH-adjusting compound is not limited and any acidic pH-adjusting compound known in the art, alone or in combination, can be used. Examples of specific acidic pH-adjusting compounds are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid.

Antioxidant

The composition may optionally include an antioxidant for improved skin condition through the removal of free radicals, and improved product stability. Some non-limiting examples of antioxidants include retinol and retinol derivatives, ascorbic acid and ascorbic acid derivatives, BHA, BHT, betacarotene, cysteine, erythorbic acid, hydroquinone, tocopherol and tocopherol derivatives, and the like.

If an antioxidant is included, it is preferably present in the composition in an amount from about 0.001 to about 2 wt. %, from about 0.01 to about 1 wt. %, and from about 0.05 to about 0.5 wt. %.

Fragrance

The composition may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synthetic ester fragrances include benzyl acetate, 4-t-butyl-cyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

The composition may include a mixture of fragrances including a mixture of natural and synthetic fragrances. The fragrance can be present in a composition in an amount up to about 5 wt. %, preferably from 0 to about 3 wt. %, from about 0 to about 1 wt. %, and from about 0 to about 0.2 wt. %.

Dye

The composition may optionally include a dye. Examples of dyes include any water soluble or product soluble dye, any FD&C or D&C approved dye.

Form of the Compositions

The compositions of the invention may be provided as a water thin liquid, structured liquid or emulsion. The composition is preferably provided as a ready to use composition, meaning that the composition is provided in a way that can be applied without needing to dilute it first.

Methods of Making the Compositions

The compositions of to the invention are easily produced by any of a number of known art techniques. Conveniently, a part of the water is supplied to a suitable mixing vessel further provided with a stirrer or agitator, and while stirring, the remaining constituents are added to the mixing vessel, including any final amount of water needed to provide to 100% wt. of the inventive composition.

The compositions may be packaged in any suitable container particularly flasks or bottles, including squeeze-type or pump bottles, as well as bottles provided with a spray apparatus (e.g. trigger spray) which is used to dispense the composition by spraying. The selected packaging may have a pump head foamer. Examples of commercially available pump head foamers include the F2 foamer from Rexam PLC (London, England, formerly Airspray), and the RF-17 Palm Foamer from Rieke Corporation (Auburn, Ind.). Accordingly the compositions are desirably provided as a ready to use product in a manually operated dispensing container.

The composition may be provided in various packaging sizes. Examples of packaging sizes include 1.5 oz, 500 ml and 1 liter bottles.

Whereas the compositions of the present invention are intended to be used in the types of liquid forms described, nothing in this specification shall be understood as to limit the use of the composition according to the invention with a further amount of water to form a solution there from. Conversely, nothing in the specification shall be also understood to limit the forming of a "super-concentrated" composition based upon the composition described above Such a super-concentrated ingredient composition is essentially the same as the compositions described above except in that they include a lesser amount of water.

Methods Employing the Sanitizing Compositions

The invention includes a method for reducing the population of a microorganism on skin, a method for treating a disease of skin, and the like. These methods can operate by contacting the body with a composition of the invention. Contacting can include any of numerous methods for applying a composition of the invention, such as spraying the compositions, immersing, foam or gel treating the skin with the composition, or a combination thereof.

The compositions of the invention can be included in any skin application products such, sanitizers, deodorizers, antiseptics, fungicides, germicides, virucides, waterless hand sanitizers, and pre- or post-surgical scrubs, preoperative skin preps.

The present invention will now be further illustrated by way of the following non-limiting examples.

EXAMPLES

The foregoing summary, detailed description, and examples provide a sound basis for understanding the invention, and some specific example embodiments of the invention. Since the invention can comprise a variety of embodiments, the above information is not intended to be limiting. The invention resides in the claims.

Formula Comparisons (used in Panel and Clinical Testing)

| Material | Test Product A | NTF-1 | NTF-2 |
| --- | --- | --- | --- |
| Ethanol, SDA 40B | 73.0 | 73.0 | 73.0 |
| VITAMIN E ACETATE (COND) | 0.10 | 0.10 | 0.10 |
| Lactic acid (COND) | | 0.05 | 0.05 |
| Gluconic Acid 50% (COND) | 0.10 | | |
| Bisabolol (COND) | 0.10 | 0.10 | 0.10 |
| Glycerine 99.5%, USP (COND) | 0.30 | 0.30 | 0.10 |
| Nicotinamide (COND) | 0.20 | 0.20 | 0.20 |
| Glycine USP (COND) | 0.17 | 0.10 | 0.10 |
| Proline (COND) | | 0.10 | 0.10 |
| Ethylhexylglycerin (MED) | 0.40 | 0.40 | 0.40 |
| C12-15 alkyl benzoate (MED) | 0.20 | 0.20 | 0.20 |
| Dicaprylyl Carbonate DRM (HIGH) | 0.10 | 0.10 | 0.10 |
| 2-propylheptyl Caprylate (HIGH) | 0.10 | 0.10 | 0.10 |

-continued

| Material | Test Product A | NTF-1 | NTF-2 |
|---|---|---|---|
| PEG 10 Dimethicone (LOW) | 2.40 | 2.40 | 2.40 |
| Potassium Hydroxide, 45% | 0.017 | 0.03 | 0.03 |
| USP Purified Water | 22.81 | 22.82 | 23.02 |
| RT solubility | S | S | S |
| Freeze/Thaw | S | S | S |

Market Leading Nourishing Foam

Active Ingredient
Ethyl Alcohol 70% v/v
Inactive Ingredients
Water (Aqua), Isopropyl Alcohol, Glycerin, PEG-12 Dimethicone, Caprylyl Glycol, Hydroxyethyl Urea, Isopropyl Myristate, Tocopheryl Acetate
Low Spreading Oil: PEG-12 Dimethicone
Medium Spreading Oil: Isopropyl Myristate
High Spreading Oil: None Example 1

Product Feel and Gloving

Healthcare workers were recruited to participate in the study, there were 45 total participants.
Products:
TEST PRODUCT A
MLNF=Market Leading Nourishing Foam
Testing Procedure:
1. The participants washed their hand with a bland hand soap and then thoroughly dried their hands with a paper towel.
2. Participants then took one application of product from a touch free dispenser (~0.7 mL) and rubbed their hands together until dry.
3. Participants then recorded their observations on product feel during application and after feel.
4. Two additional product applications were made ensure that the participant's hands were dry between applications.
5. Following the third product application, the participants applied a nitrile glove to their non-writing hand.
6. Once gloving was complete the participants recorded the ease of gloving on a 7 point scale and rated the product for overall product acceptance on a 9 point scale.
7. Upon completing evaluation of the first product the participants washed and dried their hands with the bland hand soap.
8. Steps 2 through 6 were then repeated for the second product.
9. Product order was randomized for the group of participants.

The results for overall acceptance were subjected to statistical analysis with a general linear model. Grouping Information Using Tukey Method and 95.0% Confidence. Table 1 shows a summary:

TABLE 1

| Product | N | Mean | Grouping |
|---|---|---|---|
| Test Product A | 45 | 7.1 | A |
| MLNF | 45 | 6.0 | B |

Figure 1:
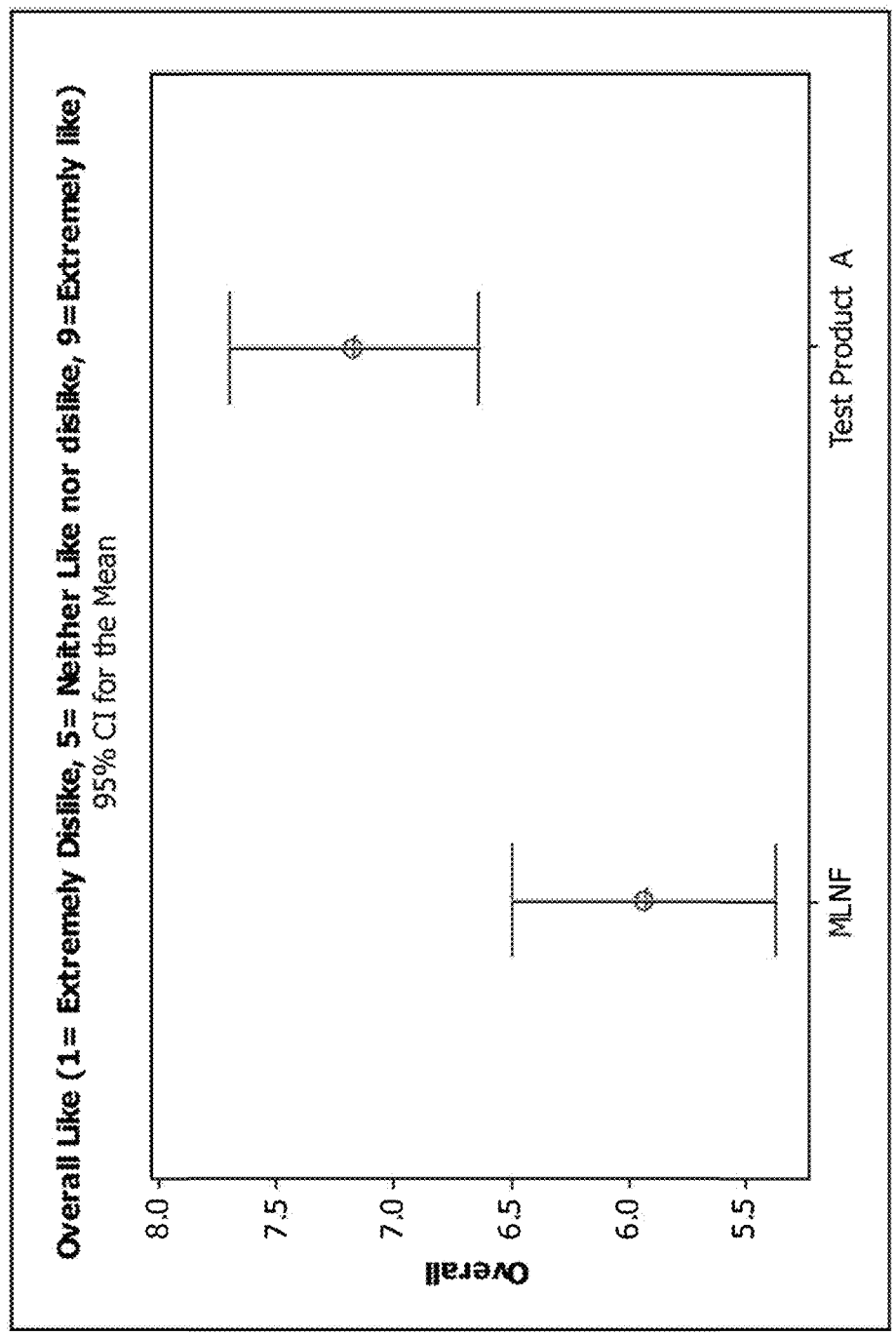
FIG. 1 is a graph of the overall product acceptance by nurses comparing a sanitizer of the invention with a commercially available product formulated to improve skin health with higher levels of moisturizers. One can see that the composition of the invention had a statistically significant increase in overall product acceptance vs. the commercial product with higher levels of moisturizers.

Means that do not share a letter are significantly different. The results are depicted graphically in FIG. 1. There was a statistically significant increase in overall product acceptance for the product of the invention.

Next gloving results were subjected to a General Linear Model: Gloving versus Participant, Product numb, Order. Grouping Information Using Tukey Method and 95.0% Confidence. A summary of the results are depicted in Table 2.

TABLE 2

| Product | N | Mean | Grouping |
|---|---|---|---|
| Test Product A | 44 | 6.1 | A |
| MLNF | 45 | 5.2 | B |

Figure 2:
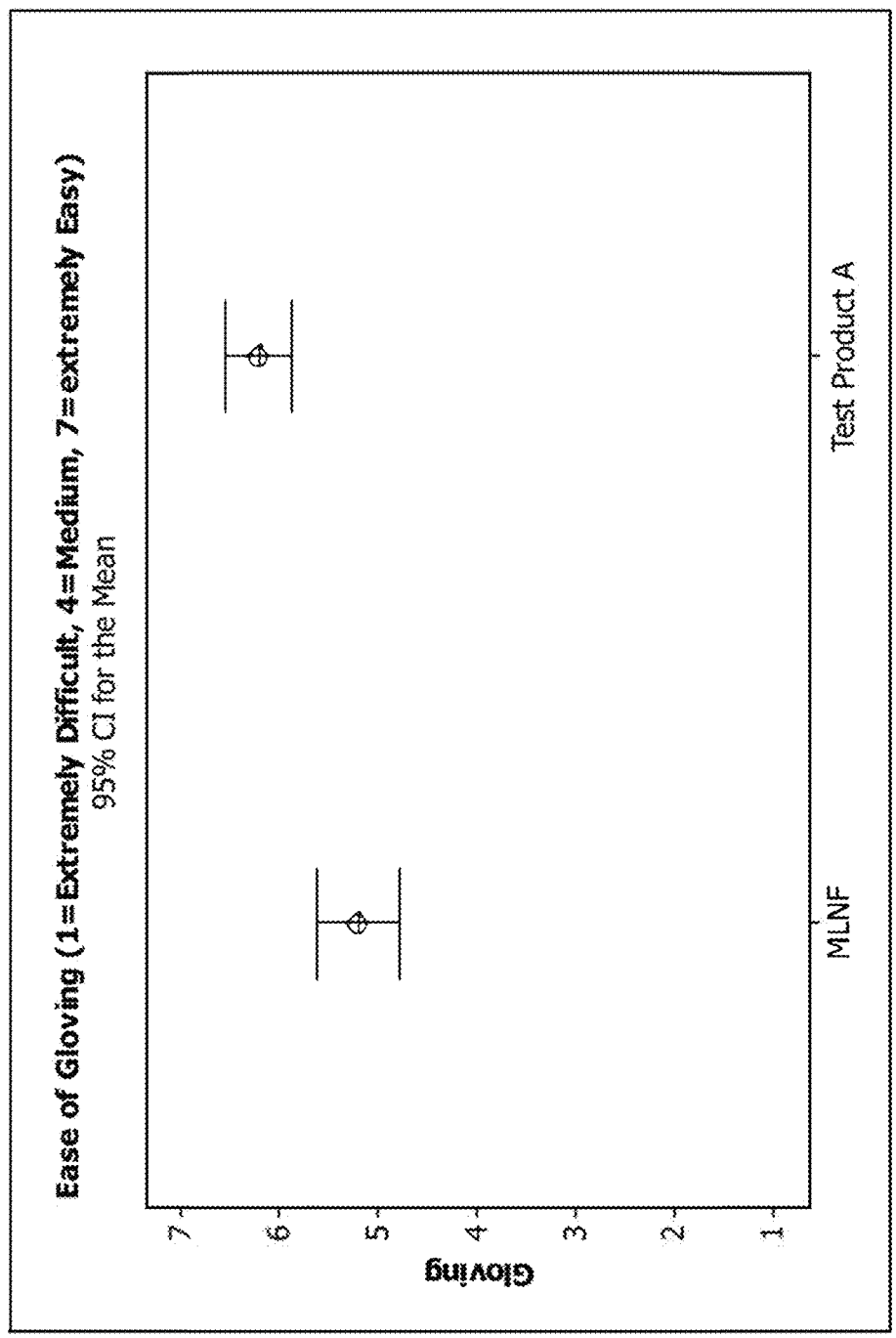
FIG. 2 is a graph showing ease of gloving from the same test as FIG. 1. From the results again, one can see that the composition of the invention resulted in easier gloving that the commercially available product with higher levels of moisturizers.

Means that do not share a letter are significantly different. The results are shown graphically in FIG. 2. From the results again, one can see that the composition of the invention resulted in statistically significantly easier gloving that the commercially available product.

Example 2

Forearm Controlled Application Test

Initial Test subjects: 45
Products:
 Nourishing Test Formula 1 (NTF 1)
 Nourishing Test Formula 2 (NTF 2)
 MLNF=Market Leading Nourishing Foam
Treatments:
 Untreated Skin
 Nourishing Test formula 1 (NTF 1)
 Nourishing test formula 2 (NTF 2)
 Market Leading Nourishing Foam
Testing Methods:
Corneometer (skin moisture)
Visual dryness (graded by an expert grader using magnification and a 5 point scale)
Tewa meter (Trans Epidermal Water Loss)
Procedure:
Sites were selected on the forearm of each test subject and 1.25" circles were marked. The product application to the site was randomized at the beginning of the study. Baseline readings were made prior to product application.
 1. Product was applied to the appropriate position on the forearm twice a day. A minimum of three hours was maintained between treatments with one site left untreated.
 2. The two applications a day was conducted for four continuous days.
 3. On the fifth day a single application was made.
 4. Once a minimum of three hours had passed following the single application on the fifth day, the final readings were made.
  Use of Test Product #1, 62% (w/w) Ethanol, was not statistically different from the untreated control in terms of erythema, dryness, skin moisture content, or transepidermal water loss.

Use of Test Product #2, 62% (w/w) Ethanol, was not statistically different from the untreated control in terms of erythema, dryness, or skin moisture content, but was statistically different from the control in terms of transepidermal water loss.

Results were subjected to statistical analysis General Linear Model: vis-dry versus test material, subject. Grouping Information Using Tukey Method and 95.0% Confidence. A summary of the results is shown in table 3.

TABLE 3

| test material | N | Mean | Grouping |
|---|---|---|---|
| NTF 2 | 46 | 0.1 | A |
| Untreated Control | 47 | 0.0 | A |
| NTF 1 | 47 | 0.0 | A |
| MLNF | 47 | −0.1 | A |

Means that do not share a letter are significantly different. None of the composition had statistically different change in visual dryness. The results are depicted graphically in FIG. 3.

Next the results for visual redness were subjected of statistical analysis. General Linear Model: vis erythema versus test material, subject.
Grouping Information Using Tukey Method and 95.0% Confidence. A summary of the results are shown in Table 4.

TABLE 4

| test material | N | Mean | Grouping |
|---|---|---|---|
| Untreated Control | 47 | 0.2 | A |
| NTF 1 | 47 | 0.1 | A |
| MLNF | 47 | 0.1 | A |
| NTF 2 | 47 | 0.1 | A |

Means that do not share a letter are significantly different.

The results are depicted graphically in FIG. 4. Here again all of the products were statistically similar despite the fact that the compositions of the invention had less skin conditioning components.

Next the results of the corneometer test were subjected to statistical analysis. General Linear Model: Corneometer versus subject_1, treatment. Grouping Information Using Tukey Method and 95.0% Confidence. The results are shown in Table 5.

TABLE 5

| Treatment | N | Mean | Grouping |
|---|---|---|---|
| MLNF | 47 | 8.1 | A |
| NTF 2 | 47 | 1.1 | B |
| Untreated Skin | 47 | 0.5 | B |
| NTF 1 | 47 | −0.3 | B |

Means that do not share a letter are significantly different. One can see the composition of the invention had similar moisture readings to untreated skin while the commercially available product had statistically significant changing in skin moisture as measured by the corneometer. The results are shown graphically in FIG. 5.

Next the transepidermal water loss was measured and the results were subjected to statistical evaluation. One-way ANOVA: TEWL versus treatment, Grouping Information Using Tukey Method. The results are shown in Table 6.

TABLE 6

| treatment | N | Mean | Grouping |
|---|---|---|---|
| NTF-1 | 47 | 3.174 | A |
| NTF-2 | 47 | 2.628 | A B |
| Untreated Skin | 46 | 1.489 | B C |
| MLNF | 47 | 1.255 | C |

Means that do not share a letter are significantly different.
Tukey 95% Simultaneous Confidence Intervals
All Pairwise Comparisons among Levels of treatment
Individual confidence level=98.98%
The results are shown graphically in FIG. 6. Both compositions of the invention were statistically significantly different than the commercial nourishing formula.

Example 3

Leg Controlled Application Test

Initial Test subjects: 38
Products:
  Test Product A (Test product, SNF)
  Market Leading Foam Sanitizer, MLFS
  Antibacterial Foaming Hand Soap (AB Soap)
Treatments:
  Untreated Skin
  AB Soap and water three times per day
  MLFS 30 times per day with 3 AB Soap and water washes
  SNF 30 times per day with 3 AB Soap and water washes
Testing Methods:
Corneometer (skin moisture)
Visual dryness (graded by an expert grader using magnification and a 5 point scale)
Procedure:
Subjects were selected for the study by having mildly dry skin as determined by an expert grader. Two sites on the back of each leg were marked. The product application to the site was randomized at the beginning of the study. Baseline readings were made prior to product application.
 1. Wash three sites with AB Soap and water, leave one site untreated.
 2. Apply 10 applications of product (either MLFS or SNF to their respective sites).
 3. Wash the three sites again with AB Soap and water.
 4. Apply 10 more applications of product.
 5. Wash the three sites again with AB Soap and Water.
 6. Apply 10 more applications of product.
Measurements and observations were made after five days of testing; the subjects then went two day without product application. The process was repeated for a total of three consecutive weeks (15 days of product application total).

Visual Dryness

FIG. 7 is a graph of the results of the leg controlled application test showing visual dryness. One can see that the product of the invention even at 30 times a day washing was most similar to untreated skin while both commercial sanitizers showed great change in dryness.

No statistical difference was observed between the untreated skin and SNF over the three weeks of the study. Both Untreated skin and SNF had statistically significant lower change from baseline visual dryness than both AB Soap and MLFS over all three weeks of the study.

Corneometer (Skin Moisture by Capacitance)

FIG. 8 is a graph of the results of the leg controlled application test showing dryness measured with a corneometer (skin moisture by capacitance). Here again the results show that the composition of the invention demonstrated higher moisture content than skin treated with either of the commercial compositions.

Example 4

Participants: 27
TGS-A and TGS-B were test products and TEST PRODUCT B is an inline hand sanitizer. Competitive Alcohol Gel B and Market Leading Competitive Gel A were competitive products. Participants tested two products per visit. Products were compared in a paired comparison test with the order randomized. All combinations were tested in a complete block design. Mini-Tab was used to calculate statistical significance.

Procedure:
1. Wash hands with the plain soap provided, then dry hands thoroughly with paper towels.
2. Apply one dose of product from the indicated bottle to your hand and observe the gel quality.
3. Rub product into your hands until your hands are dry.
4. Repeat application of the product for a total of five (be sure to mark the appropriate row for question 5 after each product application is dry, and let the assistant know if at any point you feel the need to wash your hands (after any application is dry, question 6).
5. After the fifth application is dry, put on a glove and answer question 18 on ease of gloving.
6. Answer the remaining questions (up to question 19-21) on the product evaluation questionnaire.
7. Repeat the procedure to evaluate the next product.

Question asked about gloving:

| 1 | 2 | 3 | 4 | 5 | 6 | 7 | 8 | 9 |
|---|---|---|---|---|---|---|---|---|
| No Resistance | | Slight Resistance | | Moderate Resistance | | Heavy Resistance | | Extreme Resistance |

Results:

| | TGS-A | TGS-B | Market Leading Competitive Gel A | Competitive Gel B | TEST PRODUCT B |
|---|---|---|---|---|---|
| Ease of Gloving | 1.40 A | 1.43 A | 2.39 B | 2.32 B | 2.31 B |

Results that share a letter are not statistically significantly different. Results that do not share a letter are statistically significantly different.

Example 5

Participants: 36
TEST PRODUCT C was the test product and TEST PRODUCT B is an inline hand sanitizer. Purell Advanced Instant Hand Sanitizer was the market leading competitive product. Participants tested two products per test. Two tests were conducted in one day. Products were compared in a paired comparison test with the order randomized. Mini-Tab was used to calculate statistical significance.

Comparison's made:
TEST PRODUCT C vs. TEST PRODUCT B
TEST PRODUCT C vs. Market Leading Competitive Gel A Procedure:
1. Wash hands with the plain soap provided, then dry hands thoroughly with paper towels.
2. Apply one dose of product from the indicated bottle to your hand and observe the gel quality.
3. Rub product into your hands until your hands are dry.
4. Repeat application of the product for a total of three applications. Answer appropriate questions.
5. After the third application is dry, put on a glove and answer the question on ease of gloving.
6. Answer the remaining questions on the product evaluation questionnaire.
7. Repeat the procedure to evaluate the next product.

Question asked in the trial: Please rate the ease of putting on the glove (not at all easy=1, extremely easy=7).

Ease of Gloving

| | TEST PRODUCT C | Market Leading Competitive Gel A | TEST PRODUCT B |
|---|---|---|---|
| Product Pair 1 | 6.083 A | | 4.556 B |
| Product Pair 2 | 6.000 A | 4.750 B | |

Means that do not share a letter are significantly different.

Gel Formulas

| Oil type | Ingredient | TGS-A | TGS-B | Test Product C | T Test Product B |
|---|---|---|---|---|---|
| | water | 17.12 | 16.72 | 16.940 | 22.4365 |
| | acrylates/c10-30 alkyl acrylate crosspolymer | 0.23 | 0.23 | 0.27 | 0.365 |
| high spreading | Dimethicone (6cst) | 0.25 | 0.25 | 0.25 | |
| low spreading | PEG-32 Methyl ether dimeticone | 0.25 | 0.25 | | |
| medium spreading | c12-15 alkyl benzoate | 0.25 | 0.25 | 0.25 | |
| low spreading | Cetearyl Methicone | 0.25 | 0.25 | 0.27 | |
| | ethylhexyl glycerin | 0.25 | 0.25 | 0.25 | |
| | ethanol (SD40A) | 81.00 | 81.00 | 81.00 | 73.00 |
| | vitamin E | 0.15 | 0.15 | 0.10 | |
| | Glycerin | | 0.3 | 0.30 | 0.5 |
| high spreading | Dicaprylyl Carbonate | | 0.1 | 0.10 | |
| | Tetrahydroxypropyl ethylenediamine | 0.25 | 0.25 | 0.27 | 0.425 |
| | ALOE VERA Gel, dehydr | | | | 0.0025 |
| | Titanium Dioxide | | | | 0.01 |
| medium spreading | Isopropyl Palmitate | | | | 0.25 |
| high spreading | Cyclomethicone | | | | 0.5 |
| low spreading | Polydimethyl Siloxane Emulsion >90% | | | | 0.05 |
| | VITAMIN E ACETATE liq, Cosmet. | | | | 0.05 |
| low spreading | Meadow foam Seed Oil | | | | 0.4 |
| | D-Panthenol 75W | | | | 0.001 |
| low spreading | Cetyl Alcohol | | | 0.25 | 1 |

-continued

| Oil type | Ingredient | TGS-A | TGS-B | Test Product C | T Test Product B |
|---|---|---|---|---|---|
| low spreading | Polyethylene Glycol 1450 | | | | 1 |
| | Fragrance A | | | | 0.005 |
| | Fragrance B | | | | 0.005 |
| | Fragrance C | | | 0.0075 | |

In Line Product
Low Spreading Oil: Meadow foam seed oil, polyethylene glycol 1450, cetyl alcohol, and polydimethyl siloxane emulsion (2.45% w/w)
Medium Spreading Oil: Isopropyl palmitate (0.25% w/w total)
High Spreading Oil: Cyclomethicone (0.5% w/w total)

Market Leading Competitive Gel A

| Active ingredient | Purpose |
|---|---|
| Ethyl alcohol 70% | Antimicrobial |

Inactive ingredients: Water (Aqua), Isopropyl Alcohol, Caprylyl Glycol, Glycerin, Isopropyl Myristate, Tocopheryl Acetate, Acrylates/C10-30 Alkyl Acrylate Crosspolymer, Aminomethyl Propanol, Fragrance (Parfum)
Low Spreading Oil: None
Medium Spreading Oil: Isopropyl Myristate
High Spreading Oil: None Competitive Gel B Active Ingredient
Ethyl alcohol 85%
Inactive Ingredients
Acrylates/C10-30 Alkyl Acrylate Crosspolymer, Bisabolol, Cyclomethicone, Glycerin, Isohexadecane, Myristyl Alcohol, PVP, Tetrahydroxypropyl Ethylenediamine, Water
Low Spreading Oil: Myristyl Alcohol
Medium Spreading Oil: None
High Spreading Oil: Cyclomethicone, Isohexadecane Example 6

Participants: 30
NTF-2, NTF-1, Market Leading Nourishing Foam (MLNF) were compared in a complete block design. Products were tested as pairs and the one pair was tested per day.
  1. Wash your hands with the provided mild soap.
  2. Apply one dose of product from the touch free dispenser to your hand and observe foam quality.
  3. Rub product into your hands until your hands are dry.
  4. Repeat applications for a total of five (be sure to mark the appropriate row for questions one and two after each product application is dry).
  5. After the fifth application put on a pair of gloves provided and record the difficulty of putting on the gloves.
  6. Answer all of the remaining questions on the product evaluation questionnaire.
  7. Wash hands with the mild soap and dry well.
  8. Repeat steps 4 through 11.

Gloving Question:
  Please rate your ability to put gloves on your hands after 5 applications of the product (Circle one).

No Resistance    Slight Resistance    Moderate Resistance    Difficult

No resistance = 1,
difficult = 4

General Linear Model: Gloving Versus Subject Numb, Product Name

Grouping Information Using Tukey Method and 95.0% Confidence

| product name | N | Mean | Grouping |
|---|---|---|---|
| MLNF | 60 | 2.4 | A |
| NTF-2 | 61 | 1.3 | B |
| NTF-1 | 61 | 1.3 | B |

Means that do not share a letter are significantly different.

What is claimed is:

1. A method for use of a liquid skin sanitizing composition comprising:
  applying said liquid skin sanitizer to the skin, wherein said liquid skin sanitizer comprises:
    a skin conditioners;
    a medium spreading emollient;
    a high spreading emollient;
    a linear or branched C1 to C6 alcohol; and
    water,
  wherein said ratio of high spreading emollient to medium spreading emollient is from about 3 to about 1 to about 1 to about 3 by weight to give a good skin feel; and
  allowing said liquid skin sanitizer to dry.

2. The method of claim 1 wherein said C1 to C6 alcohol is in an amount of from about 50 wt. % to about 90 wt. % of said composition.

3. The method of claim 1, wherein said one or more skin conditioners total no more than about 3 wt. % of said composition.

4. The method of claim 1, wherein said one or more skin conditioners total no more than about 2 wt. % of said composition.

5. The method of claim 1, wherein said one or more skin conditioners total no more than about 1 wt. % of said composition.

6. The method of claim 1 wherein each conditioner is present in an amount of no more than 1 wt. % of said composition.

7. The method of claim 1 wherein each conditioner is present in an amount of no more than 0.8 wt. % of said composition.

8. The method of claim 1 wherein each conditioner is present in an amount of no more than 0.5 wt. % of said composition.

9. The method of claim 1 wherein said ratio of high spreading emollient to medium spreading emollient is about 1:3.

10. The method of claim 1 wherein said medium spreading emollient includes one or more of: capric/caprylic triglyceride, C12-15 alkyl benzoate, capric triglyceride, caprylic triglyceride, isopropyl myristate, isopropyl palmitate, octyldodecanol, decyl oleate, cocoglycerides, ethylhexyl stearate, ceteraryl isononanoate, cetearyl ethyhexanonate, decyl cocoate, cetyl dimethicone, ethylhexyl palmitate, PPG-11 stearyl ether, PPG-15 stearyl ether, Dimethicone fluid (10-20cst), and PPG-14 butyl ether.

11. The method of claim 1 wherein said high spreading emollient includes one or more of dicaprylyl carbonate, dibutyl adipate, hexyl laurate, dicaprylyl ether, propylheptyl caprylate, 4-10 centistoke silicone oil, D4, 5, or 6 cyclic siloxane, isocetyl palmitate, hydrogenated polyisobutene, and diethylhexylcarbonate.

12. The method of claim 1 wherein said liquid skin sanitizer is in the form of a water thin liquid, a gel, an emulsion, or an aerosol foam.

13. The method of claim 1, wherein said steps of applying and drying are repeated from about 20 to 100 times a day.

14. The method of claim 1 wherein said skin does not feel sticky or tacky upon drying.

15. The method of claim 1 wherein said dry skin is easily gloved.

16. The method of claim 13 wherein said sanitized skin has improved health and moisture compared to non-treated skin that is sanitized from about 20 to 100 times a day.

17. The method of claim 1 wherein said skin conditioner is one or more of the following: alkyl benzoate, myristyl myristate, cetyl myristate, gelatin, carboxylic acid, lsactoc acid, glyceryl dioleate, methyl laurate, PPG-9 laurate, lauryl lacylate, allantoin, octyl palmitate, lanolin, propylene glycol, butylene glycol, ethylene glycol, capryltl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, gluconic acid, hydrolyzed silk protein, 1,3-propane diol, Vitamin E, nicatinamide stearyl alcohol, isopropyl palmitate, sorbitol, amino acid complexes, panthenol, Dihydroxypropyltrimonium Chloride, quaternized hydrolyzed protein such as collagen, oat, wheat, inositol, fructose, sucrose, hydrolyzed plant proteins, seaweed extract, polyethylene glycol, ammonium lactate, sodium hyaluronate, betaine, cyclic peptides, hydroxyethyl urea, agarose, urea, sodium PCA, arginine PCA, fructose, glucose, glutamic acid, glycerine, honey, lactose, maltose, polyethylene glycol, sorbitol, petrolatum, shea butter, avocado oil, balm mint oil, cod liver oil, mineral oil, trimyristin, stearyl stearate, synthetic wax, ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of glycereth-26, ethoxylated shea butter, bisabolol, panthenol and mixtures thereof.

18. The method of claim 1, wherein said liquid skin sanitizer further comprises a low spreading emollient.

19. The method of claim 18, wherein said low spreading emollient is present in an amount of up to about 5 wt. %.

20. The method of claim 1, wherein said applying and drying are performed for at least daily for at least five out of seven days.

* * * * *

UNITED STATES PATENT AND TRADEMARK OFFICE
CERTIFICATE OF CORRECTION

PATENT NO.         : 10,786,436 B2
APPLICATION NO.    : 16/435120
DATED              : September 29, 2020
INVENTOR(S)        : Joseph R. Wegner and Cheryl A. Littau Page 1 of 2

It is certified that error appears in the above-identified patent and that said Letters Patent is hereby corrected as shown below:

On the Title Page

(56) References Cited, Other Publications, Line 1:
DELETE ""Miacinamide:" before "A B"
INSERT --"Niacinamide:-- before "A B"

(57) ABSTRACT, Lines 6-7:
DELETE "skin feel with without a tacky residue upon drying." after the word "improved"
INSERT --skin feel without a tacky residue upon drying.-- after the word "improved"

In the Claims

In Column 24, Claim 10, Line 66:
DELETE "myristrate," after the first "isopropyl"
INSERT --myristate-- after the first "isopropyl"

In Column 25, Claim 10, Lines 1:
DELETE "ceteraryl" after "stearate,"
INSERT --cetearyl-- after "stearate,"

In Column 25, Claim 10, Lines 1-2:
DELETE "ethyhexanonate," before "decyl"
INSERT --ethylhexanonate-- before "decyl"

In Column 25, Claim 17, Lines 25-26:
DELETE "lsactoc acid" after "carboxylic acid,"
INSERT --lactic acid-- after "carboxylic acid,"

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,786,436 B2

<u>In Column 25, Claim 17, Line 27:</u>
DELETE "lacylate," before "allantoin,"
INSERT --lactylate-- before "allantoin,"

<u>In Column 25, Claim 17, Line 28:</u>
DELETE "capryltl" before the third "glycol,"
INSERT --caprylyl-- before the third "glycol,"

<u>In Column 26, Claim 17, Line 3:</u>
DELETE "nicatinamide" before "stearyl"
INSERT --nicotinamide-- before "stearyl"